(12) United States Patent
Konegawa et al.

(10) Patent No.: US 7,915,019 B2
(45) Date of Patent: Mar. 29, 2011

(54) PROCESSES FOR PREPARING OPTICALLY ACTIVE (S OR R)-β-AMINO ACID AND OPTICALLY ACTIVE (R OR S)-β-AMINO ACID ESTER, AND β-AMINO ACID 2-ALKOXYETHYL ESTER AND OPTICALLY ACTIVE (S OR R)-β AMINO ACID 2-ALKOXYETHYL ESTER

(75) Inventors: Tadayoshi Konegawa, Ube (JP);
Hiroyuki Miyata, Ube (JP); Yasuhito Yamamoto, Ube (JP)

(73) Assignee: UBE Industries, Ltd., Yamaguchi (JP)

( * ) Notice: Subject to any disclaimer, the term of this patent is extended or adjusted under 35 U.S.C. 154(b) by 826 days.

(21) Appl. No.: 11/664,878

(22) PCT Filed: Oct. 11, 2005

(86) PCT No.: PCT/JP2005/018699
§ 371 (c)(1),
(2), (4) Date: Oct. 23, 2007

(87) PCT Pub. No.: WO2006/038698
PCT Pub. Date: Apr. 13, 2006

(65) Prior Publication Data
US 2008/0038785 A1 Feb. 14, 2008

(30) Foreign Application Priority Data
Oct. 8, 2004 (JP) ................ 2004-296080

(51) Int. Cl.
*C12P 13/00* (2006.01)
*C07B 55/00* (2006.01)
(52) U.S. Cl. .................. 435/128; 561/401
(58) Field of Classification Search ............ None
See application file for complete search history.

(56) References Cited

U.S. PATENT DOCUMENTS

| 5,350,572 | A | 9/1994 | Savaides et al. |
| 6,869,781 | B2 * | 3/2005 | Groger et al. ............. 435/106 |
| 2004/0029236 | A1 | 2/2004 | Groger et al. |

FOREIGN PATENT DOCUMENTS

| CN | 1456676 A | 11/2003 |
| EP | 1361279 A1 | 11/2003 |
| EP | 1367129 A2 | 12/2003 |
| EP | 1621529 A1 | 2/2006 |
| JP | 2003-325195 A | 11/2003 |
| JP | 2003-325197 A | 11/2003 |
| WO | WO 2004/083163 A1 | 9/2004 |

OTHER PUBLICATIONS

Solomons, Organic Chemistry, 5th Edition, 1992, John Wiley & Sons, Inc, New York, pp. 1125-1133.*
Secundo et al, Biotechnology and Bioengineering, Optimization of Pseudomonas cepacia Lipase Preparations for Catalysis in Organic Solvents, 1999, 62(5), pp. 554-561.*
Chemistry Bulletin, May 31, 1995, entitled New Advances In the Research of Enzyme-Catalyzed Reactions in Organic Solvents—Control and Adjustment of Enzyme's Catalytic Activity and Selectivity (and partial translation).
Chinese Office Action issued Sep. 25, 2009, in CN-200580034133.
Database XP-002548656, Sep. 27, 1994, corresponding to U.S. Patent No. 5,350,572.
Database XP-002548657, Synthesis and Biological Evaluation of S-acyl-3-thiopropyl Prodrugs of N-pjosphonoacetyl-L-aspartate (PALA), Gagnard et al., European Journal of Medicinal Chemistry, 2003, vol. 38, No. 10, pp. 883-891.
European Search Report issued Oct. 14, 2009, in EP 05793727.8.
Faulconbridge SJ. et al., Tetrahedron Letters, (2000), vol. 41, pp. 2679 to 2681.
Gagnard et al., "Synthesis and biological evaluation of S-acyl-3-thiopropyl prodrugs of N-phosphonoacetyl-L-aspartate (PALA)", European Journal of Medicinal Chemistry, vol. 38, pp. 883-891, (2003).
Office Action mailed May 18, 2010 in Japanese application No. 2006-539349.

* cited by examiner

*Primary Examiner* — Paul A Zucker
(74) *Attorney, Agent, or Firm* — Birch, Stewart, Kolasch & Birch, LLP

(57) ABSTRACT

A process for preparing an optically active (S or R)-β-amino acid represented by formula (II):

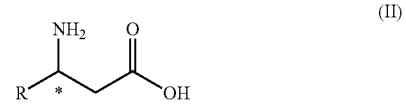

(II)

wherein R represents an alkyl group, alkenyl group, alkynyl group, cycloalkyl group, aralkyl group, aryl group or heteroaryl group each of which may have a substituent(s), and * represents an asymmetric carbon atom, and an optically active (R or S)-β-amino acid ester represented by formula (III):

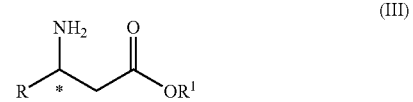

(III)

wherein R has the same meaning as defined above, $R^1$ represents an alkyl group which may have a substituent(s), and * represents an asymmetric carbon atom, provided that it has a reverse absolute configuration to that of the compound of the formula (II), which comprises selectively hydrolyzing water and one of enantiomers of a β-amino acid ester represented by formula (I):

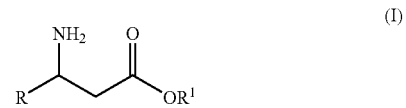

(I)

wherein R and $R^1$ have the same meanings as defined above,
which is a racemic mixture, in the presence of a hydrolase in an organic solvent.

19 Claims, No Drawings

PROCESSES FOR PREPARING OPTICALLY ACTIVE (S OR R)-β-AMINO ACID AND OPTICALLY ACTIVE (R OR S)-β-AMINO ACID ESTER, AND β-AMINO ACID 2-ALKOXYETHYL ESTER AND OPTICALLY ACTIVE (S OR R)-β AMINO ACID 2-ALKOXYETHYL ESTER

TECHNICAL FIELD

The present invention relates to a process for obtaining an optically active (S or R)-β-amino acid and an optically active (R or S)-β-amino acid ester simultaneously from a β-amino acid ester (racemic mixture), and to a novel β-amino acid 2-alkoxyethyl ester and an optically active (S or R)-β-amino acid 2-alkoxy ester which are starting materials for the above process. These optically active β-amino acid and its ester are useful as a starting material or a synthetic intermediate of a medicine, agricultural chemical such as a physiologically active peptide, a lactam series antibiotics, etc., and a physiologically active substance (for example, see Patent literatures 1-3).

BACKGROUND ART

Heretofore, as a process for preparing an optically active β-amino acid and its ester by an enantio-selective hydrolysis reaction using a biocatalyst, there has been disclosed a method in which, for example, only one of enantiomers of ethyl 3-amino-3-arylpropionate (racemic mixture) is selectively hydrolyzed in water in the presence of a lipase (trade name: Amano PS) originated from *Burkholderia cepacia* (*Pseudomonas cepacia*) to obtain an optically active (S)-3-amino-3-arylpropionic acid and an optically active (R)-ethyl 3-amino-3-arylpropionate (for example, see Non-patent literature 1.).

However, according to this method, there are problems that an E value which is an index of selectivity between enantiomers is low, when an optically active carboxylic acid which is a product is water-soluble, it is difficult to recover 100% of the product from the aqueous solution after completion of the reaction, and yet, under the presence of a large amount of water, lowering in optical purity occurs due to self-hydrolysis reaction of the substrate. Incidentally, the E value is widely utilized as an index of selectivity of kinetic optical resolution (for example, see Non-patent literature 2.).

Also, as a method for obtaining an optically active 3-amino-3-arylpropionic acid, it has been known a method to accomplish a good yield and good optical purity by making an ester portion propyl ester (for example, see Patent literature 4).

However, according to this method, a large amount of water must be used so that there are problems that the operations for the reaction become complicated since it is essential to adjust pH of an aqueous phase, etc. Incidentally, as a required optically active β-amino acid ester, a methyl ester or an ethyl ester thereof is desired in many cases, so that the resulting optically active β-amino acid propyl ester is required to be led to a desired methyl ester or ethyl ester by transesterification, etc., so that this is not an efficient method.

Moreover, as a method for obtaining an optically active 3-amino-3-arylpropionic acid, it has been known a method which can realize high enantio-selectivity by carrying out enzymatic hydrolysis of 3-amino-3-arylpropionic acid ester (racemic compound) in two-phase system of water and an organic solvent (for example, see Patent literature 5).

However, in this method, when an optically active carboxylic acid which is a product is water-soluble, it is difficult to recover the product with 100% from the aqueous solution after completion of the reaction. Also, there was a problem that in the presence of a large amount of water, lowering in optical purity was caused due to self-hydrolysis of the substrate.

Non-patent literature 1: Tetrahedron Lett., 41, 2679 (2000)

Non-patent literature 2: J. Am. Chem. Soc., 104, 7294 (1982)

Non-patent literature 3: "Chemical Dictionary", Published by Tokyo Kagaku Dojin Shuppan, p. 948 (2000)

Patent literature 1: WO 2004/092116 Publication

Patent literature 2: US 2003/0199692 Publication

Patent literature 3: WO 2001/042192 Publication

Patent literature 4: Japanese Unexamined Patent Publication No. 2003-325195

Patent literature 5: Japanese Unexamined Patent Publication No.2003-325197

DISCLOSURE OF THE INVENTION

Problems to be Solved by the Invention

An object of the present invention is to solve the above-mentioned problems, and to provide a process for preparing an optically active (S or R)-β-amino acid and an optically active (R or S)-β-amino acid ester simultaneously from β-amino acid ester (racemic mixture) by hydrolysis (reaction of β-amino acid ester (racemic mixture) and water) using an enzyme with a simple and easy method and with a high E value.

Means to Solve the Problems

Heretofore, a preparation of an optically active β-amino acid by enantio-selective hydrolysis of a β-amino acid ester (racemic mixture) is generally carried out by a method in which a large amount of water and a racemic mixture β-amino acid ester are reacted in the presence of a hydrolase in a solvent mainly comprising water. This is because in the hydrolysis of racemic mixture β-amino acid ester which is a substrate, it has been considered that the reaction proceeds rapidly as an amount of water is as much as possible. The present inventors have earnestly investigated to solve the problems mentioned above, and as a result, they have found a novel reactin system in which yield, selectivity, operability, etc. are improved as compared with the prior art technique, and superior as an industrial preparation process, in which self-hydrolysis which causes lowering in optical purity of a substrate (β-amino acid ester) which is easily hydrolyzed by water can be substantially completely inhibited, and an optically active β-amino acid which can be difficultly obtained solely due to water-solubility in general can be completely recovered by reacting water and a β-amino acid ester (racemic mixture) in the presence of a hydrolase in an organic solvent.

That is, the present invention relates to a process for preparing an optically active (S or R)-β-amino acid (hereinafter sometimes referred to as Compound (II)) represented by the formula (II):

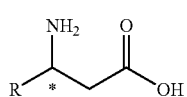

(II)

wherein R represents an alkyl group, alkenyl group, alkynyl group, cycloalkyl group, aralkyl group, aryl group or heteroaryl group each of which may have a substituent(s), and * represents an asymmetric carbon atom, and an optically active (R or S)-β-amino acid ester (hereinafter sometimes referred to as Compound (III)) represented by the formula (III):

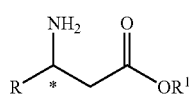

(III)

wherein R has the same meaning as defined above, $R^1$ represents an alkyl group which may have a substituent(s), and * represents an asymmetric carbon atom, provided that it has a reverse absolute configuration to that of the compound of the formula (II), which comprises selectively reacting water and one of enantiomers of a β-amino acid ester (hereinafter sometimes referred to as Compound (I)) represented by the formula (I):

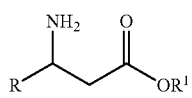

(I)

wherein R and $R^1$ have the same meanings as defined above, which is a racemic mixture, in the presence of a hydrolase in an organic solvent.

BEST MODE FOR CARRYING OUT THE INVENTION

R in Compound (I) represents an alkyl group, alkenyl group, alkynyl group, cycloalkyl group, aralkyl group, aryl group or heteroaryl group each of which may have a substituent(s).

The alkyl group of an alkyl group which may have a substituent(s) in the R is a straight or branched alkyl group having 1 to 10 carbon atoms, and may include, for example, an alkyl group such as a methyl group, ethyl group, propyl group, butyl group, pentyl group, hexyl group, heptyl group, octyl group, nonyl group and decyl group, etc., preferably a methyl group, ethyl group, n-propyl group, isopropyl group, n-butyl group or n-octyl group, more preferably a methyl group or ethyl group. Incidentally, these groups contain various kinds of isomers.

The substituent(s) in the alkyl group which may have a substituent(s) may be mentioned, for example, a halogen atom such as a fluorine atom, chlorine atom, bromine atom, iodine atom, etc.; a hydroxyl group; an alkoxyl group having 1 to 4 carbon chains such as a methoxyl group, ethoxyl group, propoxyl group, butoxyl group, etc.; an amino group; a dialkylamino group such as a dimethylamino group, diethylamino group, etc.; a cyano group; and a nitro group, etc., preferably a fluorine atom, chlorine atom, hydroxyl group, amino group or dialkylamino group.

Examples of an alkyl group having such a substituent(s) may be mentioned, for example, a fluoromethyl group, chloromethyl group, hydroxymethyl group, methoxymethyl group, aminomethyl group, dimethylaminomethyl group, 2-chloroethyl group, 2,2-dichloroethyl group, 2-hydroxyethyl group and 2-cyanoethyl group, etc., preferably a fluoromethyl group, chloromethyl group, hydroxymethyl group, aminomethyl group, dimethylaminomethyl group, 2-chloroethyl group or 2-cyanoethyl group.

The alkenyl group of an alkenyl group which may have a substituent(s) in the R is an alkenyl group having 2 to 10 carbon atoms, and may include, for example, a vinyl group, propenyl group, butenyl group, pentenyl group, hexenyl group, heptenyl group, octenyl group, nonenyl group and decenyl group, etc., preferably a vinyl group, propenyl group, butenyl group or pentenyl group, more preferably a vinyl group, 1-propenyl group or 2-propenyl group. Incidentally, these groups contain various kinds of isomers.

The substituent(s) in the alkenyl group which may have a substituent(s) may be mentioned, for example, a halogen atom such as a fluorine atom, chlorine atom, bromine atom, iodine atom, etc.; a hydroxyl group; an alkoxyl group having 1 to 4 carbon atoms such as a methoxyl group, ethoxyl group, propoxyl group, butoxyl group, etc.; an amino group; a dialkylamino group such as a dimethylamino group, diethylamino group, etc.; a cyano group; and a nitro group, etc., preferably a fluorine atom, chlorine atom, hydroxyl group, amino group or dialkylamino group.

Examples of an alkenyl group having such a substituent(s) may be mentioned, for example, a 1-fluoroethenyl group, 1-chloroethenyl group, 1-hydroxyethenyl group, 1-methoxyethenyl group, 1-aminoethenyl group, 1-cyanoethenyl group, 2-fluoroethenyl group, 2-chloroethenyl group, 2-hydroxyethenyl group, 2-methoxyethenyl group, 2-aminoethenyl group, 2-cyanoethenyl group, 1,2-dimethylaminoethenyl group, 1-fluoro-2-propenyl group, 1-chloro-2-propenyl group, 1-hydroxy-2-propenyl group, 1-methoxy-2-propenyl group, 1-amino-2-propenyl group, 1-cyano-2-propenyl group, 3-fluoro-1-propenyl group, 3-chloro-1-propenyl group, 3-hydroxy-2-propenyl group, 3-methoxy-2-propenyl group, 3-amino-2-propenyl group, 2-cyano-2-propenyl group, 3,3-dimethylamino-2-propenyl group and 3,3-dichloro-2-propenyl group, etc., preferably a 1-fluoroethenyl group, 1-chloroethenyl group, 1-hydroxyethenyl group, 1-aminoethenyl group, 1-cyanoethenyl group, 1-fluoro-2-propenyl group, 1-chloro-2-propenyl group or 1-cyano-2-propenyl group.

The alkynyl group of an alkynyl group which may have a substituent(s) in the R is an alkynyl group having 2 to 10 carbon atoms, and may include, for example, an ethynyl group, propynyl group, butynyl group, pentynyl group, hexynyl group, heptynyl group, octynyl group, nonynyl group and decynyl group, etc., preferably an ethynyl group, propynyl group, butynyl group or pentynyl group, more preferably an ethynyl group, 1-propynyl group or 2-propynyl group. Incidentally, these groups contain various kinds of isomers.

The substituent(s) in the alkynyl group which may have a substituent(s) may be mentioned, for example, a halogen atom such as a fluorine atom, chlorine atom, bromine atom, iodine atom, etc.; a hydroxyl group; an alkoxyl group having 1 to 4 carbon chains such as a methoxyl group, ethoxyl group, propoxyl group, butoxyl group, etc.; an amino group; a dialkylamino group such as a dimethylamino group, diethylamino group, etc.; a cyano group; and a nitro group, etc., preferably a fluorine atom, chlorine atom, hydroxyl group, amino group or dialkylamino group.

Examples of an alkynyl group having-such a substituent(s) may be mentioned, for example, a 2-fluoroethynyl group, 2-chloroethynyl group, 2-hydroxyethynyl group, 2-methoxyethynyl group, 2-aminoethynyl group, 2-cyanoethynyl group, 1-fluoro-2-propynyl group, 1-chloro-2-propynyl group, 1-hydroxy-2-propynyl group, 1-methoxy-2-propynyl group, 1-amino-2-propynyl group, 1-cyano-2-propynyl group, 1,1-dichloro-2-propynyl group and 1,1-diamino-2-propynyl group, etc., preferably a 2-fluoroethynyl group, 2-chloroethynyl group, 2-hydroxyethynyl group, 2-aminoethynyl group, 1-fluoro-2-propynyl group or 1,1-dichloro-2-propynyl group.

The cycloalkyl group of a cycloalkyl group which may have a substituent(s) in the R is a cycloalkyl group having 3 to 10 carbon atoms, and may include, for example, a cyclopropyl group, cyclobutyl group, cyclopentyl group, cyclohexyl group, cycloheptyl group, cyclooctyl group, cyclononyl group and cyclodecyl group, etc. (incidentally, these groups contain various kinds of isomers), preferably a cyclopropyl group, cyclobutyl group, cyclopentyl group, cyclohexyl group, cycloheptyl group or cyclooctyl group, more preferably a cyclopropyl group, cyclobutyl group, cyclopentyl group or cyclohexyl group.

The substituent(s) in the cycloalkyl group which may have a substituent(s) may be mentioned an alkyl group having 1 to 6 carbon chains, a halogen atom such as a fluorine atom, chlorine atom, bromine atom and iodine atom, etc.; a hydroxyl group; an alkoxyl group having 1 to 4 carbon chains such as a methoxyl group, an ethoxyl group, a propoxyl group and a butoxyl group, etc.; an amino group; a dialkylamino group such as a dimethylamino group and diethylamino group, etc.; a cyano group; and a nitro group, etc., preferably a fluorine atom, chlorine atom, hydroxyl group, amino group or dialkylamino group.

Examples of a cycloalkyl group having such a substituent(s) may be mentioned, for example, a 1-fluorocyclopropyl group, 2-fluorocyclopropyl group, 3-fluorocyclobutyl group, methoxycyclopropyl group, aminocyclopentyl group, dimethylaminocyclohexyl group, 2-chlorocyclopropyl group, 2,2-dichlorocyclohexyl group, 2-hydroxycyclobutyl group and 2-cyanocyclohexyl group, etc., preferably a fluorocyclopropyl group or chlorocyclobutyl group.

The aralkyl group of an aralkyl group which may have a substituent(s) in the R may include, for example, an aralkyl group such as a benzyl group, phenethyl group, phenylpropyl group and phenylbutyl group, etc., preferably a benzyl group, 1-phenethyl group, 2-phenethyl group, 3-phenylpropyl group or 3-phenylbutyl group. Incidentally, these groups contain various kinds of isomers.

The substituent(s) in the aralkyl group which may have a substituent(s) may be mentioned, for example, an alkyl group having 1 to 10 carbon atoms such as a methyl group, ethyl group, propyl group, butyl group, pentyl group, hexyl group, heptyl group, octyl group, nonyl group, and decyl group, etc. (incidentally, these groups contain various kinds of isomers.); a hydroxyl group; a nitro group; a halogen atom such as a fluorine atom, chlorine atom, bromine atom and iodine atom, etc.; an alkoxyl group having 1 to 10 carbon atoms such as a methoxyl group, ethoxyl group, propoxyl group, butoxyl group, pentyloxyl group, hexyloxyl group, heptyloxyl group, octyloxyl group, nonyloxyl group and decyloxyl group, etc. (incidentally, these groups contain various kinds of isomers.); an aralkyloxyl group having 7 to 10 carbon atoms such as a benzyloxyl group, phenethyloxyl group and phenylpropoxyl group, etc. (incidentally, these groups contain various kinds of isomers.); an aryloxyl group such as a phenyloxyl group and naphthyloxyl group, etc. (incidentally, these groups contain various kinds of isomers.); an alkoxyalkoxyl group such as methoxymethoxyl group and methoxyethoxyl group, etc. (incidentally, these groups contain various kinds of isomers.); a monoalkylamino group such as a methylamino group and ethylamino group, etc. (incidentally, these groups contain various kinds of isomers.); a dialkylamino group such as a dimethylamino group and diethylamino group, etc. (incidentally, these groups contain various kinds of isomers.); an acylamino group such as a formyl-amino group, acetylamino group and benzoylamino group, etc. (incidentally, these groups contain various kinds of isomers.); a nitro group; a cyano group; and a halogenated alkyl group such as a trifluoromethyl group, and the like.

Examples of an aralkyl group having such a substituent(s) may be mentioned, for example, a 2-fluorobenzyl group, 3-fluorobenzyl group, 4-fluorobenzyl group, 3,4-difluorobenzyl group, 2,4-difluorobenzyl group, 2-chlorobenzyl group, 3-chlorobenzyl group, 4-chlorobenzyl group, 2,4-dichlorobenzyl group, 3,4-dichlorobenzyl group, 2-bromobenzyl group, 3-bromobenzyl group, 4-bromobenzyl group, 2,4-dibromobenzyl group, 3,4-dibromobenzyl group, 2-iodobenzyl group, 3-iodobenzyl group, 4-iodobenzyl group, 2,3-diiodobenzyl group, 3,4-diiodobenzyl group, 2-methylbenzyl group, 3-methylbenzyl group, 4-methylbenzyl group, 2-ethylbenzyl group, 3-ethylbenzyl group, 4-ethylbenzyl group, 2-hydroxybenzyl group, 3-hydroxybenzyl group, 4-hydroxybenzyl group, 2-methoxybenzyl group, 3-methoxybenzyl group, 4-methoxybenzyl group, 2,4-dimethoxybenzyl group, 3,4-dimethoxybenzyl group, 2-ethoxybenzyl group, 4-ethoxybenzyl group, 2-trifluoromethylbenzyl group, 4-trifluoromethylbenzyl group, 4-benzyloxybenzyl group, 2-nitrobenzyl group, 3-nitrobenzyl group, 4-nitrobenzyl group, 2-cyanobenzyl group, 3-cyanobenzyl group, 4-cyanobenzyl group, 4-dimethylaminobenzyl group, 4-formylaminobenzyl group, 2-acetylaminobenzyl group, 3-acetylaminobenzyl group, 4-acetylaminobenzyl group, 4-benzoylaminobenzyl group, 2-(2-fluorophenyl)ethyl group, 2-(3-fluorophenyl)ethyl group, 2-(4-fluorophenyl)ethyl group, 2-(3,4-difluorophenyl)ethyl group, 2-(2,4-difluorophenyl)ethyl group, 2-(2-chlorophenyl)ethyl group, 2-(3-chlorophenyl)ethyl group, 2-(4-chlorophenyl)ethyl group, 2-(2,4-dichlorophenyl)ethyl group, 2-(3,4-dichlorophenyl)ethyl group, 2-(2-bromophenyl)ethyl group, 2-(3-bromophenyl)ethyl group, 2-(4-bromophenyl)ethyl group, 2-(2,4-dibromophenyl)ethyl group, 2-(3,4-dibromophenyl)ethyl group, 2-(2-iodophenyl)ethyl group, 2-(3-iodophenyl)ethyl group, 2-(4-iodophenyl)ethyl group, 2-(2,3-diiodophenyl)ethyl group, 2-(3,4-diiodophenyl)ethyl group, 2-(2-tolyl)ethyl group, 2-(3-tolyl)ethyl group, 2-(4-tolyl)ethyl group, 2-(2-ethylphenyl)ethyl group, 2-(3-ethylphenyl)ethyl group, 2-(4-ethylphenyl)ethyl group, 2-(2-hydroxyphenyl)ethyl group, 2-(4-hydroxyphenyl)ethyl group, 2-(2-methoxyphenyl)ethyl group, 2-(3-methoxyphenyl)ethyl group, 2-(4-methoxyphenyl)ethyl group, 2-(2,4-dimethoxyphenyl)ethyl group, 2-(3,4-dimethoxyphenyl)ethyl group, 2-(2-ethoxyphenyl)ethyl group, 2-(4-ethoxyphenyl)ethyl group, 2-(2-trifluoromethylphenyl)ethyl group, 2-(4-trifluoromethylphenyl)ethyl group, 2-(4-benzyloxyphenyl)ethyl group, 2-(2-nitrophenyl)ethyl group, 2-(3-nitrophenyl)ethyl group, 2-(4-nitrophenyl)ethyl group, 2-(2-cyanophenyl)ethyl group, 2-(3-cyanophenyl)ethyl group, 2-(4-cyanophenyl)ethyl group, 2-(4-dimethylaminophenyl)ethyl group, 2-(4-formylaminophenyl)ethyl group, 2-(2-acetylaminophenyl)ethyl group, 2-(3-acetylaminophenyl)ethyl group, 2-(4-acetylaminophenyl)ethyl group, 2-(4-benzoylaminophenyl)ethyl group, 3-(2-fluorophenyl)propyl group, 3-(4-fluorophenyl)propyl group, 3-(4-chlorophenyl)propyl group, 3-(4-bromophenyl)propyl group, 3-(4-iodophenyl)propyl group, 3-(2-chlorophenyl)propyl group, 3-(2-methoxyphenyl)propyl group, 3-(4-methoxyphenyl)propyl group, 3-(3,4-dimethoxyphenyl)propyl group, 3-(4-trifluoromethylphenyl)propyl group, 3-(2-trifluoromethylphenyl)propyl group, 3-(4-nitrophenyl)propyl group, 3-(4-cyanophenyl)propyl group and 3-(4-acetylaminophenyl)propyl group, etc., preferably a 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2-methylbenzyl group, 3-methylbenzyl group, 4-methylbenzyl group, 2-hydroxybenzyl group, 4-hydroxybenzyl group, 2-methoxybenzyl group, 3-methoxybenzyl group, 4-methoxybenzyl group, 3,4-dimethoxybenzyl group, 2-trifluoromethylbenzyl group, 4-trifluoromethylbenzyl group, 4-benzyloxybenzyl group, 2-nitrobenzyl group, 3-nitrobenzyl group, 4-nitrobenzyl group, 2-cyanobenzyl group, 3-cyanobenzyl group, 4-cyanobenzyl group, 4-formylaminobenzyl group, 3-acetylaminobenzyl group, 4-acetylaminobenzyl group, 4-benzoylaminobenzyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-(2-bromophenyl)ethyl group, 2-(3-bromophenyl)ethyl group, 2-(4-bromophenyl)ethyl group, 2-(2-iodophenyl)ethyl group, 2-(3-iodophenyl)ethyl group, 2-(4-iodophenyl)ethyl group, 2-(2-tolyl)ethyl group, 2-(3-tolyl)ethyl group, 2-(4-tolyl)ethyl group, 2-(2-ethylphenyl)ethyl group, 2-(2-hydroxyphenyl)ethyl group, 2-(4-hydroxyphenyl)ethyl group, 2-(2-methoxyphenyl)ethyl group, 2-(3-methoxyphenyl)ethyl group, 2-(4-methoxyphenyl)ethyl group, 2-(2,4-dimethoxyphenyl)ethyl group, 2-(3,4-dimethoxyphenyl)ethyl group, 2-(2-trifluoromethylphenyl)ethyl group, 2-(4-trifluoromethylphenyl)ethyl group, 2-(4-benzyloxyphenyl)ethyl group, 2-(2-nitrophenyl)ethyl group, 2-(3-nitrophenyl)ethyl group, 2-(4-nitrophenyl)ethyl group, 2-(2-cyanophenyl)ethyl group, 2-(3-cyanophenyl)ethyl group, 2-(4-cyanophenyl)ethyl group, 2-(2-acetylaminophenyl)ethyl group, 2-(3-acetylaminophenyl)ethyl group, 2-(4-acetylaminophenyl)ethyl group, 2-(4-benzoylaminophenyl)ethyl group, 3-(2-fluorophenyl)propyl group, 3-(4-fluorophenyl)propyl group, 3-(4-chlorophenyl)propyl group, 3-(4-bromophenyl)propyl group, 3-(4-iodophenyl)propyl group, 3-(2-chlorophenyl)propyl group, 3-(2-methoxyphenyl)propyl group, 3-(4-methoxyphenyl)propyl group, 3-(3,4-dimethoxyphenyl)propyl group, 3-(4-trifluoromethylphenyl)propyl group, 3-(2-trifluoromethylphenyl)propyl group, 3-(4-nitrophenyl)propyl group, 3-(4-cyanophenyl)propyl group or 3-(4-acetylaminophenyl)propyl group, more preferably (2-fluorobenzyl group, 4-fluorobenzyl group, 2-chlorobenzyl group, 4-chlorobenzyl group, 2-bromobenzyl group, 4-bromobenzyl group, 2-iodobenzyl group, 4-iodobenzyl group, 2-methylbenzyl group, 4-methylbenzyl group, 4-hydroxybenzyl group, 2-methoxybenzyl group, 4-methoxybenzyl group, 3,4-dimethoxybenzyl group, 2-trifluoromethylbenzyl group, 4-trifluoromethylbenzyl group, 4-benzyloxybenzyl group, 2-nitrobenzyl group, 4-nitrobenzyl group, 2-cyanobenzyl group, 3-cyanobenzyl group, 4-cyanobenzyl group, 3-acetylaminobenzyl group, 4-acetylaminobenzyl group, 2-(2-fluorophenyl)ethyl group, 2-(4-fluorophenyl)ethyl group, 2-(2-chlorophenyl)ethyl group, 2-(4chlorophenyl)ethyl group, 2-(2-bromophenyl)ethyl group, 2-(4-bromophenyl)ethyl group, 2-(2-iodophenyl)ethyl group, 2-(4-iodophenyl)ethyl group, 2-(2-tolyl)ethyl group, 2-(4-tolyl)ethyl group, 2-(4-hydroxyphenyl)ethyl group, 2-(2-methoxyphenyl)ethyl group, 2-(4-methoxyphenyl)ethyl group, 2-(3,4-dimethoxyphenyl)ethyl group, 2-(2-trifluoromethylphenyl)ethyl group, 2-(4-trifluoromethylphenyl)ethyl group, 2-(4-benzyloxyphenyl)ethyl group, 2-(2-nitrophenyl)ethyl group, 2-(4-nitrophenyl)ethyl group, 2-(2-cyanophenyl)ethyl group, 2-(4-cyanophenyl)ethyl group, 2-(2-acetylaminophenyl) ethyl group or 2-(4-acetylaminophenyl)ethyl group.

The aryl group of an aryl group which may have a substituent(s) in the R is an aryl group such as a phenyl group, naphthyl group, anthranyl group, phenanthryl group, biphenyl group and binaphthyl group, etc.

The substituent(s) in the aryl group which may have a substituent(s) may be mentioned an alkyl group having 1 to 4 carbon atoms such as a methyl group, ethyl group, propyl group and butyl group, etc. (incidentally, these groups contain various kinds of isomers.); a hydroxyl group; a halogen atom such as a chlorine atom, bromine atom, iodine atom and fluorine atom, etc.; an alkoxyl group having 2 to 4 carbon atoms such as an ethoxyl group, etc. (incidentally, these groups contain various kinds of isomers.); an alkylenedioxy group having 1 to 4 carbon atoms such as a methylenedioxy group, etc.; a nitro group; a cyano group; and a halogenated alkyl group such as a trifluoromethyl group, and the like.

Examples of an aryl group having such a substituent(s) may be mentioned, for example, a 2-tolyl group, 3-tolyl group, 4-tolyl group, 2,3-xylyl group, 2,6-xylyl group, 2,4-xylyl group, 3,4-xylyl group, mesityl group, 2-hydroxyphenyl group, 3-hydroxyphenyl group, 4-hydroxyphenyl group, 2,3-dihydroxyphenyl group, 2,4-dihydroxyphenyl group, 3,4-dihydroxyphenyl group, 2-chlorophenyl group, 3-chlorophenyl group, 4-chlorophenyl group, 2,3-dichlorophenyl group, 2,4-dichlorophenyl group, 3,4-dichlorophenyl group, 3,5-dichlorophenyl group, 2-bromophenyl group, 3-bromophenyl group, 4-bromophenyl group, 2-iodophenyl group, 3-iodophenyl group, 4-iodophenyl group, 2-fluorophenyl group, 3-fluorophenyl group, 4-fluorophenyl group, 2,3-difluorophenyl group, 2,4-difluorophenyl group, 3,4-difluorophenyl group, 3-bromo-5-chloro-2-hydroxyphenyl group, 2-methoxyphenyl group, 3-methoxyphenyl group, 4-methoxyphenyl group, 2,3-dimethoxyphenyl group, 2,4-dimethoxyphenyl group, 3,4-dimethoxyphenyl group, 3,5-dimethoxyphenyl group, 3,4-methylenedioxyphenyl group, 4-ethoxyphenyl group, 4-butoxyphenyl group, 4-isopropoxyphenyl group, 1-phenoxyphenyl group, 4-benzyloxyphenyl group, 4-trifluoromethylphenyl group, 2-nitrophenyl group, 3-nitrophenyl group, 4-nitrophenyl group, 4-cyanophenyl group, 4-methoxycarbonylphenyl group, 1-naphthyl group and 2-naphthyl group, etc., preferably a phenyl group, 2-tolyl group, 3-tolyl group, 4-tolyl group, 2,3-xylyl group, 2-hydroxyphenyl group, 3-hydroxyphenyl group, 4-hydroxyphenyl group, 2,3-dihydroxyphenyl group, 2,4-dihydroxyphenyl group, 3,4-dihydroxyphenyl group, 2-chlorophenyl group, 3-chlorophenyl group, 4-chlorophenyl group, 2,3-dichlorophenyl group, 2,4-dichlorophenyl group, 3,4-dichlorophenyl group, 3,5-dichlorophenyl group, 2-bromophenyl group, 3-bromophenyl group, 4-bromophenyl group, 2-iodophenyl group, 3-iodophenyl group, 4-iodophenyl group, 2-fluorophenyl group, 3-fluorophenyl group, 4-fluorophenyl group, 3,4-difluorophenyl group, 3-bromo-5-chloro-2-hydroxyphenyl group, 2-methoxyphenyl group, 3-methoxyphenyl group, 4-methoxyphenyl group, 2,3-dimethoxyphenyl group, 2,4-dimethoxyphenyl group, 3,4-dimethoxyphenyl group, 3,5-dimethoxyphenyl group, 3,4-methylenedioxyphenyl group, 4-ethoxyphenyl group, 4-trifluoromethylphenyl group, 4-nitrophenyl group, 4-cyanophenyl group, 1-naphthyl group or 2-naphthyl group, more preferably phenyl group, 2-tolyl group, 3-tolyl group, 4-tolyl group, 2,3-xylyl group, 4-hydroxyphenyl group, 3,4-dihydroxyphenyl group, 2-chlorophenyl group, 3-chlorophenyl group, 4-chlorophenyl group, 2,3-dichlorophenyl group, 2,4-dichlorophenyl group, 3,4-dichlorophenyl group, 3,5-dichlorophenyl group, 2-bromophenyl group, 3-bromophenyl group, 4-bromophenyl group, 4-iodophenyl group, 2-fluorophenyl group, 3-fluorophenyl group, 4-fluorophenyl group, 3,4-difluorophenyl group, 2-iodophenyl group, 3-iodophenyl group, 4-iodophenyl group, 2-methoxyphenyl group, 3-methoxyphenyl group, 4-methoxyphenyl group, 2,3-dimethoxyphenyl group, 2,4-dimethoxyphenyl group, 3,4-dimethoxyphenyl group, 3,5-dimethoxyphenyl group, 3,4-methylenedioxyphenyl group, 4-trifluoromethylphenyl group, 4-nitrophenyl group, 1-naphthyl group, 2-naphthyl group or 3-pyridyl group, particularly preferably a phenyl group, 2-tolyl group, 3-tolyl group, 4-tolyl group, 2,3-xylyl group, 2-chlorophenyl group, 3-chlorophenyl group, 4-chlorophenyl group, 2,3-dichlorophenyl group, 2,4-dichlorophenyl group, 3,4-dichlorophenyl group, 3,5-dichlorophenyl group, 2-bromophenyl group, 3-bromophenyl group, 4-bromophenyl group, 2-fluorophenyl group, 3-fluorophenyl group, 4-fluorophenyl group, 3,4-difluorophenyl group, 2-iodophenyl group, 3-iodophenyl group, 4-iodophenyl group, 2-methoxyphenyl group, 3-methoxyphenyl group, 4-methoxyphenyl group, 2,3-dimethoxyphenyl group, 3,4-dimethoxyphenyl group, 3,5-dimethoxyphenyl group or 3,4-methylenedioxyphenyl group.

The heteroaryl group of a heteroaryl group which may have a substituent(s) in the R may include, for example, a 2-furyl group, 3-furyl group, 2-pyridyl group, 3-pyridyl group, 4-pyridyl group, 2-pyrrolyl group, 3-pyrrolyl group, 2-thienyl group, 3-thienyl group, 2-indolyl group, 3-indolyl group, 2-imidazolyl group, 4-imidazolyl group, 3-pyrazolyl group, 2-pyrimidyl group, 4-pyrimidyl group and quinolyl group, etc.

The substituent(s) in the heteroaryl group which may have a substituent(s) may be mentioned an alkyl group having 1 to 4 carbon atoms such as a methyl group, ethyl group, propyl group and butyl group, etc. (incidentally, these groups contain various kinds of isomers.); a hydroxyl group; a halogen atom such as a chlorine atom, bromine atom, iodine atom and fluorine atom, etc.; an alkoxyl group having 2 to 4 carbon atoms such as an ethoxyl group, etc. (incidentally, these groups contain various kinds of isomers.); an amino group; a nitro group; a cyano group; and a halogenated alkyl group such as a trifluoromethyl group, and the like.

Examples of a heteroaryl group having such a substituent(s) may be mentioned, for example, a 2-(3-methyl)furyl group, 2-(4-methyl)furyl group, 2-(3-ethyl)furyl group, 2-(4-ethyl)furyl group, 2-(3-fluoro)furyl group, 2-(3-chloro)furyl group, 2-(3-hydroxy)furyl group, 2-(3-methoxy)furyl group, 2-(3-amino)furyl group, 2-(3-nitro)furyl group, 2-(3-cyano)furyl group, 2-(3-methyl)pyridyl group, 2-(4-methyl)pyridyl group, 2-(3-ethyl)pyridyl group, 2-(4-ethyl)pyridyl group, 2-(3-fluoro)pyridyl group, 2-(4-chloro)pyridyl group, 2-(3-hydroxy)pyridyl group, 2-(3-methoxy)pyridyl group, 2-(3-amino)pyridyl group, 2-(3-nitro)pyridyl group, 2-(3-cyano)pyridyl group, 2-(3,5-dichloro)pyridyl group, 3-(2-chloro)pyridyl group, 2-(3-methyl)pyrrolyl group and 2-(3-methyl)thienyl group, etc., preferably a 2-(3-methyl)furyl group, 2-(3-fluoro)furyl group, 2-(3-methyl)pyridyl group, 2-(3-fluoro)pyridyl group, 2-(3-nitro)pyridyl group, 2-(3-cyano)pyridyl group or 2-(3,5-dichloro)pyridyl group.

$R^1$ in Compound (I) represents an alkyl group which may have a substituent(s).

The alkyl group of an alkyl group which may have a substituent(s) in the $R^1$ is a straight or branched alkyl group having 1 to 10 carbon atoms, and may include, for example, a methyl group, ethyl group, propyl group, butyl group, pentyl group, hexyl group, heptyl group, octyl group, nonyl group and decyl group, preferably a methyl group, ethyl group, n-propyl group, isopropyl group, n-butyl group, isobutyl group, sec-butyl group, n-pentyl group or n-hexyl group, more preferably a methyl group, ethyl group, n-propyl group, n-butyl group or isobutyl group. Incidentally, these groups contain various kinds of isomers.

The substituent(s) in the alkyl group which may have a substituent(s) may be mentioned a halogen atom such as a fluorine atom, chlorine atom, bromine atom and iodine atom, etc.; a hydroxyl group; an alkoxyl group having 1 to 4 carbon chains such as a methoxyl group, ethoxyl group, propoxyl group and butoxyl group, etc.; a dialkylamino group such as a dimethylamino group and diethylamino group, etc.; a cyano group, etc., preferably a fluorine atom, chlorine atom, methoxyl group, ethoxyl group, hydroxyl group or cyano group, more preferably a fluorine atom, chlorine atom, methoxyl group or ethoxyl group.

Examples of an alkyl group having such a substituent(s) may be mentioned, for example, a 2-fluoroethyl group, 2-chloroethyl group, 2,2-difluoroethyl group, 2,2-dichloroethyl group, 2,2,2-trichloroethyl group, 2,2,2-trifluoroethyl group, 2-methoxyethyl group, 2-ethoxyethyl group, 2-a methoxymethyl group, 2-hydroxyethyl group, 2-cyanoethyl group, 2-bromoethyl group, 2-dimethylamino group, 2-chloropropyl group and 3-chloropropyl group, etc., preferably a 2-chloroethyl group, 2,2,2-trichloroethyl group, 2,2,2-trifluoroethyl group, a methoxymethyl group, 2-methoxyethyl group or 2-ethoxyethyl group.

As the hydrolase to be used in the reaction of the present invention, there may be mentioned, for example, protease, esterase, lipase, etc., preferably lipase obtained from microorganisms isolatable from yeast or bacteria, more preferably lipase (for example, Amano PS (available from Amano Enzyme Co.), etc.) originated from *Burkholderia cepacia* (*Pseudomonas cepacia*) is used. Incidentally, as these hydrolases, commercially available product can be used as such as a natural form or an immobilized enzyme, and may by used alone of in admixture of two or more kinds. Also, an enzyme-immobilizing agent contained in the commercially available product is previously removed and then the treated product may be used.

The above-mentioned hydrolases are desirably used after subjecting the commercially available product sold as a natural form or an immobilized enzyme to chemical treatment or physical treatment.

As the above-mentioned chemical treatment or physical treatment method, there may be specifically mentioned, for example, a method in which hydrolase is dissolved in a buffer (an organic solvent may be presented, if necessary), and used as such or stirred and lyophilized, etc. Incidentally, lyophilization is a method in which an aqueous solution and a substance containing water are freezed rapidly at a temperature not more than the freezing point, and a pressure is reduced to the water vapor pressure or lower of the freezed product to remove water by sublimation whereby drying the substance (for example, see Non-patent literature 3). Incidentally, catalytic activities (reactivity, selectivity, etc.) can be improved by the said treatment.

As the above-mentioned buffer, there may be mentioned, for example, an aqueous solution of an inorganic acid salt such as an aqueous sodium phosphate solution, an aqueous potassium phosphate solution, etc.; an aqueous solution of an organic acid salt such as an aqueous sodium acetate solution, an aqueous ammonium acetate solution, an aqueous sodium citrate solution, etc., preferably an aqueous sodium phosphate solution, an aqueous potassium phosphate solution, an aqueous ammonium acetate solution is/are used. Incidentally, these buffers may be used used singly or in admixture of two or more kinds.

A concentration of the above-mentioned buffer is preferably 0.01 to 2 mol/L, more preferably 0.05 to 0.5 mol/L, and a pH of the buffer is preferably 4 to 9, more preferably 7 to 8.5.

An amount of the buffer to be used at the time of lyophilization is not particularly limited so long as it is a concentration that the hydrolase is completely dissolved, and preferably 10 ml to 1000 ml, more preferably 10 ml to 100 ml based on 1 g of the hydrolase.

An amount of the above-mentioned hydrolase to be used is preferably 0.1 to 1000 mg, more preferably 1 to 200 mg based on 1 g of Compound (I).

The reaction of the present invention is carried out in the presence of a hydrolase in an organic solvent. During the reaction of the present invention, the hydrolase participates in the reaction by presenting a substantially suspended state in the reaction mixture, and there is no problem even when it is slightly dissolved in the mixture. Incidentally, the terms "in an organic solvent" in the present invention mean the state in which a reaction solvent to be used in the hydroloysis is an organic solvent, and a liquid portion dissolved in the organic solvent, except for the hydrolase (an immobilizing agent may be contained in some cases) and a precipitating product, etc., does not cause phase separation (that is, a state in which water (which may contain the below-mentioned inorganic said or organic salt), a substrate and an organic solvent constitute a single phase).

As the water to be used in the reaction of the present invention, purified water such as deionized water, distilled water, etc., is generally used, and it is desired that an inorganic salt such as sodium phosphate, potassium phosphate, etc., or an organic salt such as sodium acetate, ammonium acetate, sodium citrate, etc., is added to water to present them in the reaction system. An amount of these inorganic salt and organic salt to be used is preferably an amount of 0.01 to 10 mol/L based on the amount of water, more preferably 0.1 to 1 mol/L. Incidentally, the above-mentioned inorganic salt or organic salt is previously dissolved in water to prepare a buffer and the buffer may be used in the reaction.

An amount of the above-mentioned water to be used is an amount of the solubility of the organic solvent to be used or less (since if it exceeds the solubility, phase separation of the liquid portion occurs), and the upper limit may be somewhat different depending on the kind of compound (I), preferably 0.5 to 10 mol, more preferably 0.5 o 5.0 mol, particularly preferably 1.0 to 3.0 mol, further preferably 1.5 to 2.5 mol based on 1 mol of Compound (I). Incidentally, whereas it depends on the kinds of Compound (I), when the amount of water to be used exceeds 10 mol based on 1 mol of Compound (I), undesirable states occur, for example, self-hydrolysis of Compound (I) which lowers optical purity of the products, elongation of the reaction time due to becoming a suspended state (a state in which phase separation at the liquid portion occurs) in which water is not dissolved in an organic solvent with a small amount, etc. occur, so that an amount of water to be used is adjusted to the solubility of the organic solvent or less, preferably 10 mol or less.

As the above-mentioned organic solvent, there may be mentioned, for example, at least one selected from an aliphatic hydrocarbon such as n-pentane, n-hexane, n-heptane, n-octane, cyclopentane, cyclohexane and cyclopentane, etc.; an aromatic hydrocarbon such as benzene, toluene and xylene, etc.; an ether such as diethyl ether, t-butylmethyl ether, diisopropyl ether, cyclopentylmethyl ether, tetrahydrofuran and 1,4-dioxane, etc.; a ketone such as acetone and methyl ethyl ketone, etc., preferably n-hexane, n-heptane, cyclopentane, cyclohexane, toluene, diisopropyl ether, t-butylmethyl ether, cyclopentylmethyl ether and/or tetrahydrofuran, more preferably n-hexane, cyclohexane, toluene, diisopropyl ether, t-butylmethyl ether and/or cyclopentylmethyl ether, particularly preferably cyclohexane, toluene and/or t-butylmethyl ether. Incidentally, these organic solvents may be used alone or in admixture of two or more kinds.

An amount of the above-mentioned solvent to be used is preferably 2 to 200 mL, more preferably 5 to 80 mL based on 1 g of Compound (I).

The reaction of the present invention is desirably carried out in the presence of a surfactant, and the surfactant to be used may be mentioned, for example, a nonionic surfactant such as polyethylene glycol, polyvinylpyrrolidone, polyethylene lauryl ether, polyethylene cetyl ether and polyoxyethylene octylphenyl ether, etc.; an amphoteric surfactant such as 3-[(3-chloroamidopropyl)-dimethylammonio]-2-hydroxy-1-propanesulfonate and 3-[(3-chloroamidopropyl)-dimethylammonio]-1-propanesulfonate, etc.; an anionic surfactant such as sodium dioctylsulfosuccinate, sodium dodecylsulfonate and tris(hydroxymethyl)-aminomethanedodecyl sulfate, etc.; a cationic surfactant such as cetyltrimethyl ammonium bromide or cetyldimethylethyl ammonium bromide, etc., preferably nonionic surfactant, more preferably polyethylene glycol, polyethylene cetyl ether or polyoxyethylene octylphenyl ether, particularly preferably polyoxyethylene octylphenyl ether is used. Incidentally, these surfactants may be used alone or in admixture of two or more kinds.

An amount of the above-mentioned surfactant to be used is preferably 10 to 1000 mg, more preferably 50 to 200 mg based on 1 g of Compound (I).

The reaction of the present invention can be carried out, for example, by a method in which Compound (I), a hydrolase, water (if necessary, it may contain an inorganic salt or an organic salt) and an organic solvent are mixed, and they are reacted under stirring, etc. A reaction temperature at that time is preferably 0 to 80° C., more preferably 10 to 50° C., particularly preferably 30 to 45° C., and a reaction pressure is not specifically limited. Incidentally, during the reaction, the hydrolase is substantially in a suspended state, and while it may depend on a kind of Compound (II), Compound (II) sometimes precipitates as a solid as the reaction proceeds in some cases, but these suspended states or precipitation do not substantially affect on the reaction.

Compound (II) and Compound (III) obtained by the reaction of the present invention can be isolated to obtain Compound (II) by, for example, when Compound (II) is precipitated after completion of the reaction, adding a suitable organic solvent (for example, acetonitrile, acetone, etc.) to the reaction mixture, if necessary, and filtering the mixture, and to obtain Compound (III) by concentrating the organic layer. Also, after completion of the reaction, when Compound (II) is not precipitated, Compound (II) can be obtained by, for example, adjusting a pH of the mixture, extracting Compound (II) with water, further re-adjusting a pH of the aqueous layer, extracting the same with an organic solvent, and concentrating the resulting organic layer, and Compound (III) can be obtained by concentrating the organic layer separated at the time of extracting Compound (II) with water. Incidentally, the obtained Compound (II) and Compound (III) can be further purified by the general method such as crystallization, recrystallization, distillation, column chromatography, etc.

Incidentally, the β-amino acid 2-alkoxyethyl ester (hereinafter sometimes referred to as Compound (IV)) represented by the formula (IV):

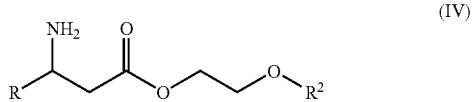

wherein R has the same meaning as defined above, and $R^2$ represents an alkyl group,
which is a racemic mixture to be used in the reaction of the present invention is a novel compound, and in the formula (IV), R is the same as those shown in Compound (I), $R^2$ is an alkyl group, specifically those of a straight or branched alkyl group having 1 to 6 carbon atoms, and there may be mentioned, for example, a methyl group, ethyl group, propyl group, butyl group, pentyl group and hexyl group, preferably a methyl group or ethyl group. Incidentally, these groups contain various kinds of isomers.

Also, an optically active (R or S)-β-amino acid 2-alkoxyethyl ester (hereinafter sometimes referred to as Compound (V)) represented by the formula (V):

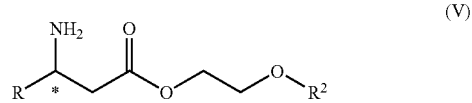

wherein R, $R^2$ and * have the same meanings as defined above,
obtained by hydrolysis is a novel compound, and in the formula (V), R, $R^2$ and * have the same meanings as those shown in Compound (I) and Compound (IV).

Incidentally, when the above-mentioned Compound (IV) is used, the desired products (Compound (V) and a corresponding carboxylic acid compound having reverse absolute configuration to that of Compound (V)) can be obtained with high yield and high E value, so that it can be said that it is an extremely useful compound.

EXAMPLE

Next, the present invention is explained more specifically by referring to Examples, but the scope of the present invention is not limited by these.

Reference Example 1 (Synthesis of 3-amino-3-phenylpropionic acid (racemic mixture))

To 250 mL of isopropyl alcohol were added 17.7 g (0.17 mol) of benzaldehyde, 18.2 g (0.17 mol) of malonic acid and 25.6 g (0.33 mol) of ammonium acetate, and the mixture was reacted under stirring and reflux (80 to 90° C.) for 7 hours. After completion of the reaction, the obtained reaction mixture was stirred at 0 to 5° C. for 1 hour, and filtered to obtain 19.2 g (Isolation yield based on benzaldehyde: 70.0%) of 3-amino-3-phenylpropionic acid (racemic mixture) as white powder.

Incidentally, physical properties of the 3-amino-3-phenylpropionic acid (racemic mixture) were as follows.

$^1$H-NMR (δ (ppm), $D_2O+DCl$): 3.06 (dd, 1H, J=17.1, 6.8 Hz), 3.17 (dd, 1H, J=17.1, 7.3 Hz), 4.76 (dd, 1H, J=7.3, 6.8 Hz), 3.77 (s, 2H), 7.45 (m, 5H)

$^{13}$C-NMR (δ (ppm), $D_2O+DCl$): 40.5, 54.4, 130.0, 132.3, 132.6, 138.0, 176.3

MS (EI) m/z: 165 ($M^+$)

MS (CI, i-$C_4H_{10}$) m/z: 166 ($MH^+$)

Elemental analysis; Calcd: C, 65.44%; H, 6.71%; N, 8.48%

Found: C, 65.18%; H, 6.78%; N, 8.34%

Reference Example 2 (Synthesis of ethyl 3-amino-3-phenylpropionate (racemic mixture))

To 6.00 mL (103 mmol) of ethanol were added 2.00 g (12.1 mmol) of 3-amino-3-phenylpropionic acid (racemic mixture) synthesized in Reference example 1 and 1.78 g (18.2 mmol) of conc. sulfuric acid, and the mixture was reacted under stirring at 60° C. for 4 hours. After completiontion of the reaction, the obtained reaction mixture was concentrated under reduced pressure, and 6 mol/L aqueous sodium hydroxide solution was added thereto to adjust a pH of the reaction mixture to 8.5. Then, 10 mL of ethyl acetate and 4 mL of water were added to the mixture to carry out extraction, and the organic layer was dried over anhydrous magnesium sulfate. After filtration, the filtrate was concentrated under reduced pressure to obtain 1.98 g (Isolation yield based on 3-amino-3-phenylpropionic acid (racemic mixture): 84.5%) of ethyl 3-amino-3-phenylpropionate (racemic mixture) as colorless liquid.

Incidentally, physical properties of the ethyl 3-amino-3-phenylpropionate (racemic mixture) were as follows.

$^1$H-NMR (δ (ppm), $CDCl_3$): 1.19 (t, 3H, J=7.3 Hz), 3.15 (dd, 1H, J=7.3, 16.6 Hz), 3.25 (dd, 1H, J=7.3, 16.6 Hz), 4.15 (q, 2H, J=7.3 Hz), 4.85 (dd, 1H, J=7.3, 7.3 Hz), 7.50-7.55 (m, 5H)

$^{13}$C-NMR (δ (ppm), $CDCl_3$): 16.0, 40.9, 54.3, 65.2, 129.9, 132.2, 132.5, 137.8, 174.3

MS (EI) m/z: 193 ($M^+$)

MS (CI, i-$C_4H_{10}$) m/z: 194 ($MH^+$)

Example 1 (Synthesis of (S)-3-amino-3-phenylpropionic acid and ethyl (R)-3-amino-3-phenylpropionate)

To 2.5 mL of t-butylmethyl ether saturated with water were added 250 mg (1.29 mmol) of ethyl 3-amino-3-phenylpropionate (racemic mixture) and 12.5 mg of lipase (Amano Lipase PS (trade name); available from Aldrich) originated from *Burkholderia cepacia* (*Pseudomonas cepacia*), and the mixture was maintained at 30° C. To the obtained mixture was added 23.3 μL of water at the same temperature, and the mixture was reacted under stirring at 30° C. for 70 hours. Amano Lipase PS was substantially in a suspended state during the reaction, and with the progress of the reaction, (S)-3-amino-3-phenylpropionic acid which is a product was precipitated as crystalline solid. After completion of the reaction, 0.5 mL of acetone was added to the reaction mixture and the mixture was filtered to obtain a mixture of 85.6 mg (Isolation yield based on ethyl 3-amino-3-phenylpropionate (racemic mixture)=40.0%) of (S)-3-amino-3-phenylpropionic acid and lipase.

The (S)-3-amino-3-phenylpropionic acid was led to n-propyl (S)-3-amino-3-phenylpropionate according to the conventional manner, and an optical purity thereof was measured by using high performance liquid chromatography which uses an optically active column, then it was 99.8% ee.

The ethyl (R)-3-amino-3-phenylpropionate was led to ethyl (R)-3-(2-furoylamino)-3-phenylpropionate according to the conventional manner, and an optical purity thereof was measured by using high performance liquid chromatography which uses an optically active column, then it was 91.8% ee.

Incidentally, the E value in the present reaction was 3291.
Analytical conditions of high performance liquid chromatography;
Optically active n-propyl 3-amino-3-phenylpropionate
Column: Chiral CD-Ph (0.46 cmΦ×25 cm, available from Shiseido Co., Ltd.)
Solvent: acetonitrile/water (=1/9 (volume ratio))
Potassium dihydrogen phosphate 40 mmol/L
Adjusted to pH 3.5 with phosphoric acid
Flow rate: 0.5 mL/min
Temperature: 30° C.
Wavelength: 220 nm
Optically active ethyl 3-(2-furoylamino)-3-phenylpropionate
Column: Chiralcel OJ-H (0.46 cmΦ×25 cm, available from Daicel Chemical Industries, Ltd.)
Solvent: hexane/isopropyl alcohol (=9/1 (volume ratio))
Flow rate: 0.5 mL/min
Temperature: 30° C.
Wavelength: 220 nm Also, physical properties of the (S)-3-amino-3-phenylpropionic acid were the same as those shown in Reference example 1, and physical properties of the ethyl (R)-3-amino-3-phenylpropionate were the same as those shown in Reference example 2.

Reference Example 3 (Synthesis of n-propyl 3-amino-3-phenylpropionate (racemic mixture))

To 6.00 mL (80.6 mmol) of n-propyl alcohol were added 2.00 g (12.1 mmol) of 3-amino-3-phenylpropionic acid (racemic mixture) synthesized in Reference example 1 and 1.78 g (18.2 mmol) of conc. sulfuric acid, and the mixture was reacted under stirring at 60° C. for 4 hours. After completion of the reaction, the obtained reaction mixture was concentrated under reduced pressure, 6 mol/L aqueous sodium hydroxide solution was added to the mixture to adjust pH of the reaction mixture to 8.5. Then, 10 mL of ethyl acetate and 4 mL of water were added to the mixture to extract the same, and the organic layer was dried over anhydrous magnesium sulfate. After filtration, the filtrate was concentrated under reduced pressure to obtain 2.16 g (Isolation yield based on 3-amino-3-phenylpropionic acid (racemic mixture): 86.1%) of n-propyl 3-amino-3-phenylpropionate (racemic mixture) as colorless liquid.

Incidentally, physical properties of the n-propyl 3-amino-3-phenylpropionate (racemic mixture) are as follows.

$^1$H-NMR (δ (ppm), CDCl$_3$): 0.90 (d, 3H, J=7.3 Hz), 1.55-1.65 (tq, 2H, J=7.3, 6.8 Hz), 2.63 (d, 2H, J=6.8 Hz), 4.01 (t, 2H, J=6.8 Hz), 4.39 (d, 1H, J=6.8 Hz), 7.20-7.35 (m, 5H)

$^{13}$C-NMR (δ (ppm), CDCl$_3$): 10.4, 21.9, 44.2, 52.7, 66.1, 126.2, 127.3, 128.6, 144.7, 172.0

MS (EI) m/z: 207 (M$^+$)
MS (CI, i-C$_4$H$_{10}$) m/z: 208 (MH$^+$)
Elemental analysis; Calcd: C, 69.54%; H, 8.27%; N, 6.76%
Found: C, 68.86%; H, 8.22%; N, 6.60%

Example 2 (Synthesis of (S)-3-amino-3-phenylpropionic acid and n-propyl (R)-3-amino-3-phenylpropionate)

To 2.0 mL of t-butylmethyl ether to which water had been saturated were added 200 mg (0.965 mmol) of n-propyl 3-amino-3-phenylpropionate (racemic mixture) and 10.0 mg of lipase (Amano Lipase PS (trade name); available from Aldrich) originated from *Burkholderia cepacia* (*Pseudomonas cepacia*), and the mixture was maintained at 30° C. To the resulting mixture was added 17.4 μL of water at the same temperature, and the mixture was reacted under stirring at 30° C. for 70 hours. Amano Lipase PS was substantially suspended state during the reaction, and with the progress of the reaction, (S)-3-amino-3-phenylpropionic acid which is a product was precipitated as a crystalline solid. After completion of the reaction, 0.5 mL of acetone was added to the reaction mixture and the resulting mixture was filtered to obtain a mixture containing 65.2 mg (Isolation yield based on n-propyl 3-amino-3-phenylpropionate (racemic mixture)= 41.0%) of (S)-3-amino-3-phenylpropionic acid and lipase.

The (S)-3-amino-3-phenylpropionic acid was led to n-propyl (S)-3-amino-3-phenylpropionate according to the conventional manner, and an optical purity thereof was measured by using high performance liquid chromatography which uses an optically active column, then it was 99.8% ee.

The n-propyl (R)-3-amino-3-phenylpropionate was led to n-propyl (R)-3-(2-furoylamino)-3-phenylpropionate according to the conventional manner, and an optical purity thereof was measured by using high performance liquid chromatography which uses an optically active column, then it was 75.6% ee.

Incidentally, the E value in the present reaction was 2291.
Analytical conditions of high performance liquid chromatography;
Optically active n-propyl 3-amino-3-phenylpropionate
Column: Chiral CD-Ph (0.46 cmΦ×25 cm, available from Shiseido Co., Ltd.)
Solvent: acetonitrile/water (=1/9 (volume ratio))
Potassium dihydrogen phosphate 40 mmol/L
Adjusted to pH 3.5 with phosphoric acid
Flow rate: 0.5 mL/min
Temperature: 30° C.
Wavelength: 220 nm
Optically active n-propyl 3-(2-furoylamino)-3-phenylpropionate
Column: Chiralcel OJ-H (0.46 cmΦ×25 cm, available from Daicel Chemical Industries, Ltd.)
Solvent: hexane/isopropyl alcohol (=9/1 (volume ratio))
Flow rate: 0.5 mL/min
Temperature: 30° C.
Wavelength: 220 nm Also, physical properties of the (S)-3-amino-3-phenylpropionic acid were the same as those shown in Reference example 1, and physical properties of the n-propyl (R)-3-amino-3-phenylpropionate were the same as those shown in Reference example 3.

Reference Example 4 (Synthesis of 2-methoxyethyl 3-amino-3-phenylpropionate (racemic mixture))

To 6.00 mL (76.3 mmol) of 2-methoxyethanol were added 2.00 g (12.1 mmol) of 3-amino-3-phenylpropionic acid (racemic mixture) synthesized in Reference example 1 and 1.78 g (18.2 mmol) of conc. sulfuric acid, and the mixture was reacted under stirring at 60° C. for 4 hours. After completion of the reaction, the resulting reaction mixture was concentrated under reduced pressure, and then, 6 mol/L aqueous sodium hydroxide solution was added to the reaction mixture to adjust a pH thereof to 8.5. Then, 10 mL of ethyl acetate and 4 mL of water were added to the mixture to carry out extraction, and the organic layer was dried over anhydrous magnesium sulfate. After filtration, the filtrate was concentrated under reduced pressure to obtain 2.22 g (Isolation yield based on 3-amino-3-phenylpropionic acid (racemic mixture): 82.2%) of 2-methoxyethyl 3-amino-3-phenylpropionate (racemic mixture) as colorless liquid.

Incidentally, 2-methoxyethyl 3-amino-3-phenylpropionate (racemic mixture) is a novel compound shown by the following physical properties.

$^1$H-NMR (δ (ppm), CDCl$_3$): 2.711 (d, 1H, J=7.8 Hz), 2.714 (d, 1H, J=5.9 Hz), 3.37 (s, 3H), 3.57 (t, 2H, J=4.9 Hz), 4.25 (t, 2H, J=4.9 Hz), 4.43 (dd, 1H, J=5.9, 7.8 Hz), 7.24-7.38 (m, 5H)

$^{13}$C-NMR (δ (ppm), CDCl$_3$): 44.2, 52.7, 59.0, 63.5, 70.4, 126.2, 127.4, 128.6, 144.7, 172.0

MS (EI) m/z: 223 (M$^+$)

MS (CI, i-C$_4$H$_{10}$) m/z: 224 (MH$^+$)

Example 3 (Synthesis of 2-methoxyethyl (S)-3-amino-3-phenylpropionic acid and (R)-3-amino-3-phenylpropionate)

To 2.0 mL of t-butylmethyl ether to which water had been saturated were added 200 mg (0.896 mmol) of 2-methoxyethyl 3-amino-3-phenylpropionate (racemic mixture) and 10.0 mg of lipase (Amano Lipase PS (trade name); available from Aldrich) originated from *Burkholderia cepacia* (*Pseudomonas cepacia*), and the mixture was maintained at 30° C. To the resulting mixture was added 16.1 μL of water at the same temperature, and the mixture was reacted under stirring at 30° C. for 18 hours. Amano Lipase PS was substantially suspended state during the reaction, and with the progress of the reaction, (S)-3-amino-3-phenylpropionic acid which is a product was precipitated as a crystalline solid. After completion of the reaction, 0.5 mL of acetone was added to the reaction mixture and the resulting mixture was filtered to obtain a mixture containing 60.7 mg (Isolation yield based on 2-methoxyethyl 3-amino-3-phenylpropionate (racemic mixture)=41.0%) of (S)-3-amino-3-phenylpropionic acid and lipase.

The (S)-3-amino-3-phenylpropionic acid was led to n-propyl (S)-3-amino-3-phenylpropionate according to the conventional manner, and an optical purity thereof was measured by using high performance liquid chromatography which uses an optically active column, then it was 99.8% ee.

The 2-methoxyethyl (R)-3-amino-3-phenylpropionate was led to 2-methoxyethyl (R)-3-benzoylamino-3-phenylpropionate according to the conventional manner, and an optical purity thereof was measured by using high performance liquid chromatography which uses an optically active column, then it was 92.2% ee.

Incidentally, the E value in the present reaction was 2970.

Analytical conditions of high performance liquid chromatography;

Optically active n-propyl 3-amino-3-phenylpropionate

Column: Chiral CD-Ph (0.46 cmΦ×25 cm, available from Shiseido Co., Ltd.)

Solvent: acetonitrile/water (=1/9 (volume ratio))
 Potassium dihydrogen phosphate 40 mmol/L
 Adjusted to pH 3.5 with phosphoric acid Flow rate: 0.5 mL/min Temperature: 30° C.

Wavelength: 220 nm

Optically active 2-methoxyethyl 3-benzoylamino-3-phenylpropionate

Column: Chiralcel OJ-H (0.46 cmΦ×25 cm, available from Daicel Chemical Industries, Ltd.)

Solvent: hexane/isopropyl alcohol (=8/2 (volume ratio))

Flow rate: 0.5 mL/min

Temperature: 30° C.

Wavelength: 220 nm

Also, physical properties of the (S)-3-amino-3-phenylpropionic acid were the same as those shown in Reference example 1, and physical properties of the 2-methoxyethyl (R)-3-amino-3-phenylpropionate were the same as those shown in Reference example 4.

Example 4 (Synthesis of (S)-3-amino-3-phenylpropionic acid and ethyl (R)-3-amino-3-phenylpropionate)

To 2.0 mL of t-butylmethyl ether to which water had been saturated were added 200 mg (1.03 mmol) of ethyl 3-amino-3-phenylpropionate (racemic mixture) and 10.0 mg of lipase (Amano Lipase PS (trade name); available from Aldrich) originated from *Burkholderia cepacia* (*Pseudomonas cepacia*), and the mixture was maintained at 30° C. To the resulting mixture was added 18.6 μL of 0.2 mol/L phosphate buffer (phosphate buffer solution in which 1 mol/L aqueous potassium hydroxide solution was added to 0.2 mol/L aqueous potassium dihydrogen phosphate solution to adjust a pH thereof to 8.2) at the same temperature, and the mixture was reacted under stirring at 30° C. for 66 hours. Amano Lipase PS was substantially suspended state during the reaction, and with the progress of the reaction, (S)-3-amino-3-phenylpropionic acid which is a product was precipitated as a crystalline solid. After completion of the reaction, 0.5 mL of acetone was added to the reaction mixture and the resulting mixture was filtered to obtain a mixture containing 68.7 mg (Isolation yield based on ethyl 3-amino-3-phenylpropionate (racemic mixture)=40.2%) of (S)-3-amino-3-phenylpropionic acid and lipase.

The (S)-3-amino-3-phenylpropionic acid was led to n-propyl (S)-3-amino-3-phenylpropionate according to the conventional manner, and an optical purity thereof was measured by using high performance liquid chromatography which uses an optically active column, then it was 99.9% ee.

The ethyl (R)-3-amino-3-phenylpropionate was led to ethyl (R)-3-(2-furoylamino)-3-phenylpropionate according to the conventional manner, and an optical purity thereof was measured by using high performance liquid chromatography which uses an optically active column, then it was 90.6% ee.

Incidentally, the E value in the present reaction was 5012.

Analytical conditions of high performance liquid chromatography;

Optically active n-propyl 3-amino-3-phenylpropionate

Column: Chiral CD-Ph (0.46 cmΦ×25 cm, available from Shiseido Co., Ltd.)

Solvent: acetonitrile/water (=1/9 (volume ratio))
 Potassium dihydrogen phosphate 40 mmol/L
 Adjusted to pH 3.5 with phosphoric acid Flow rate: 0.5 mL/min Temperature: 30° C.

Wavelength: 220 nm

Optically active ethyl 3-(2-furoylamino)-3-phenylpropionate

Column: Chiralcel OJ-H (0.46 cmΦ×25 cm, available from Daicel Chemical Industries, Ltd.)

Solvent: hexane/isopropyl alcohol (=9/1 (volume ratio))

Flow rate: 0.5 mL/min

Temperature: 30° C.

Wavelength: 220 nm

Also, physical properties of the (S)-3-amino-3-phenylpropionic acid were the same as those shown in Reference example 1, and physical properties of the ethyl (R)-3-amino-3-phenylpropionate were the same as those shown in Reference example 2.

Example 5 (Syntheses of (S)-3-amino-3-phenylpropionic acid and ethyl (R)-3-amino-3-phenylpropionate)

To 2.0 mL of t-butylmethyl ether to which water had been saturated were added 200 mg (1.03 mmol) of ethyl 3-amino-3-phenylpropionate (racemic mixture), 20 µL of a surfactant (Triton X-100 (trade name)) and 18.6 µL of water, and the mixture was maintained at 30° C. To the resulting mixture was added 10.0 mg of lipase (Amano Lipase PS (trade name); available from Aldrich) originated from *Burkholderia cepacia* (*Pseudomonas cepacia*) at the same temperature, and the mixture was reacted under stirring at 30° C. for 42 hours. Amano Lipase PS was substantially suspended state during the reaction, and with the progress of the reaction, (S)-3-amino-3-phenylpropionic acid which is a product was precipitated as a crystalline solid. After completion of the reaction, 0.5 mL of acetone was added to the reaction mixture and the resulting mixture was filtered to obtain a mixture containing 68.4 mg (Isolation yield based on ethyl 3-amino-3-phenylpropionate (racemic mixture)=40.0%) of (S)-3-amino-3-phenylpropionic acid and lipase.

The (S)-3-amino-3-phenylpropionic acid was led to n-propyl (S)-3-amino-3-phenylpropionate according to the conventional manner, and an optical purity thereof was measured by using high performance liquid chromatography which uses an optically active column, then it was 99.9% ee.

The ethyl (R)-3-amino-3-phenylpropionate was led to ethyl (R)-3-(2-furoylamino)-3-phenylpropionate according to the conventional manner, and an optical purity thereof was measured by using high performance liquid chromatography which uses an optically active column, then it was 96.5% ee.

Incidentally, the E value in the present reaction was 8169.
Analytical conditions of high performance liquid chromatography;
Optically active n-propyl 3-amino-3-phenylpropionate
Column: Chiral CD-Ph (0.46 cmΦ×25 cm, available from Shiseido Co., Ltd.)
Solvent: acetonitrile/water (=1/9 (volume ratio))
  Potassium dihydrogen phosphate 40 mmol/L
  Adjusted to pH 3.5 with phosphoric acid
Flow rate: 0.5 mL/min
Temperature: 30° C.
Wavelength: 220 nm
Optically active ethyl 3-amino-3-(2-furoylamino)-3-phenylpropionate
Column: Chiralcel OJ-H (0.46 cmΦ×25 cm, available from Daicel Chemical Industries, Ltd.)
Solvent: hexane/isopropyl alcohol (=9/1 (volume ratio))
Flow rate: 0.5 mL/min
Temperature: 30° C.
Wavelength: 220 nm Also, physical properties of the (S)-3-amino-3-phenylpropionic acid were the same as those shown in Reference example 1, and physical properties of the ethyl (R)-3-amino-3-phenylpropionate were the same as those shown in Reference example 2.

Reference Example 4 (Chemical Treatment of Lipase)

To 50 mL of 0.1 mol/L phosphate buffer (phosphate buffer solution in which 0.1 mol/L aqueous disodium hydrogen phosphate solution was added to 0.1 mol/L aqueous potassium dihydrogen phosphate solution to adjust a pH thereof to 7.0) was added 5.00 g of lipase (Amano Lipase PS (trade name); available from Aldrich) originated from *Burkholderia cepacia* (*Pseudomonas cepacia*), and the mixture was stirred at room temperature. After 30 minutes, the mixture was filtered under reduced pressure and the resulting filtrate was lyophilized (freeze dried) to obtain 1.50 g of chemically treated lipase as green powder.

Example 6 (Synthesis of (S)-3-amino-3-phenylpropionic acid and ethyl (R)-3-amino-3-phenylpropionate)

To 2.0 mL of t-butylmethyl ether to which water had been saturated were added 200 mg (1.03 mmol) of ethyl 3-amino-3-phenylpropionate (racemic mixture), 5 mg of diatomaceous earth and 18.6 µL of water, and the mixture was maintained at 30° C. To the resulting mixture was added 10.0 mg of the chemically treated lipase prepared in Reference example 4 at the same temperature, and the mixture was reacted under stirring at 30° C. for 40 hours. Amano Lipase PS was substantially suspended state during the reaction, and with the progress of the reaction, (S)-3-amino-3-phenylpropionic acid which is a product was precipitated as a crystalline solid. After completion of the reaction, 0.5 mL of acetone was added to the reaction mixture and the resulting mixture was filtered to obtain a mixture containing 69.7 mg (Isolation yield based on ethyl 3-amino-3-phenylpropionate (racemic mixture)=40.8%) of (S)-3-amino-3-phenylpropionic acid and lipase.

The (S)-3-amino-3-phenylpropionic acid was led to n-propyl (S)-3-amino-3-phenylpropionate according to the conventional manner, and an optical purity thereof was measured by using high performance liquid chromatography which uses an optically active column, then it was 99.9% ee.

The ethyl (R)-3-amino-3-phenylpropionate was led to ethyl (R)-3-(2-furoylamino)-3-phenylpropionate according to the conventional manner, and an optical purity thereof was measured by using high performance liquid chromatography which uses an optically active column, then it was 95.7% ee.

Incidentally, the E value in the present reaction was 6947.
Analytical conditions of high performance liquid chromatography;
Optically active n-propyl 3-amino-3-phenylpropionate
Column: Chiral CD-Ph (0.46 cmΦ×25 cm, available from Shiseido Co., Ltd.)
Solvent: acetonitrile/water (=1/9 (volume ratio))
  Potassium dihydrogen phosphate 40 mmol/L
  Adjusted to pH 3.5 with phosphoric acid
Flow rate: 0.5 mL/min
Temperature: 30° C.
Wavelength: 220 nm
Optically active ethyl 3-(2-furoylamino)-3-phenylpropionate
Column: Chiralcel OJ-H (0.46 cmΦ×25 cm, available from Daicel Chemical Industries, Ltd.)
Solvent: hexane/isopropyl alcohol (=9/1 (volume ratio))
Flow rate: 0.5 mL/min
Temperature: 30° C.
Wavelength: 220 nm Also, physical properties of the (S)-3-amino-3-phenylpropionic acid were the same as those mentioned in Reference example 1.

Physical properties of the ethyl (R)-3-amino-3-phenylpropionate were the same as those mentioned in Reference example 2.

Example 7 (Synthesis of (S)-3-amino-3-phenylpropionic acid and ethyl (R)-3-amino-3-phenylpropionate)

To 2.0 mL of t-butylmethyl ether to which water had been saturated were added 200 mg (1.03 mmol) of ethyl 3-amino- 3-phenylpropionate (racemic mixture) and 10.0 mg of the chemically treated lipase prepared in Reference example 4, and the mixture was maintained at 30° C. To the resulting mixture were added 20 μL of a surfactant (Triton X-100 (trade name)) and 18.6 μL of water at the same temperature, and the mixture was reacted under stirring at 30° C. for 28 hours. With the progress of the reaction, (S)-3-amino-3-phenylpropionic acid which is a product was precipitated as a crystalline solid. After completion of the reaction, 0.5 mL of acetone was added to the reaction mixture and the resulting mixture was filtered to obtain a mixture containing 69.3 mg (Isolation yield based on ethyl 3-amino-3-phenylpropionate (racemic mixture)=40.5%) of (S)-3-amino-3-phenylpropionic acid and lipase.

The (S)-3-amino-3-phenylpropionic acid was led to n-propyl (S)-3-amino-3-phenylpropionate according to the conventional manner, and an optical purity thereof was measured by using high performance liquid chromatography which uses an optically active column, then it was 99.9% ee.

The ethyl (R)-3-amino-3-phenylpropionate was led to ethyl (R)-3-(2-furoylamino)-3-phenylpropionate according to the conventional manner, and an optical purity thereof was measured by using high performance liquid chromatography which uses an optically active column, then it was 89.0% ee.

Incidentally, the E value in the present reaction was 6007. Analytical conditions of high performance liquid chromatography;
Optically active n-propyl 3-amino-3-phenylpropionate
Column: Chiral CD-Ph (0.46 cmΦ×25 cm, available from Shiseido Co., Ltd.)
Solvent: acetonitrile/water (=1/9 (volume ratio))
  Potassium dihydrogen phosphate 40 mmol/L
  Adjusted to pH 3.5 with phosphoric acid
Flow rate: 0.5 mL/min
Temperature: 30° C.
Wavelength: 220 nm
Optically active ethyl 3-(2-furoylamino)-3-phenylpropionate
Column: Chiralcel OJ-H (0.46 cmΦ×25 cm, available from Daicel Chemical Industries, Ltd.)
Solvent: hexane/isopropyl alcohol (=9/1 (volume ratio))
Flow rate: 0.5 mL/min
Temperature: 30° C.
Wavelength: 220 nm Also, physical properties of the (S)-3-amino-3-phenylpropionic acid were the same as those shown in Reference example 1, and physical properties of the ethyl (R)-3-amino-3-phenylpropionate were the same as those shown in Reference example 2.

Reference Example 5 (Synthesis of 3-amino-3-(4-tolyl)propionic acid (racemic mixture))

To 250 mL of ethanol were added 50.0 g (0.42 mol) of 4-tolylaldehyde, 47.6 g (0.46 mol) of malonic acid and 64.2 g (0.83 mol) of ammonium acetate, and the mixture was reacted under stirring and reflux (80 to 90° C.) for 7.5 hours. The resulting reaction mixture was stirred at 0 to 5° C. for 30 minutes and then filtered to obtain 51.4 g (Isolation yield based on 4-tolylaldehyde: 68.9%) of 3-amino-3-(4-tolyl)propionic acid (racemic mixture) as white powder.

Incidentally, physical properties of the 3-amino-3-(4-tolyl)propionic acid (racemic mixture) were as follows.
$^1$H-NMR (δ (ppm), D$_2$O+DCl): 2.30 (s, 3H), 3.04 (dd, 1H, J=17.1, 6.8 Hz), 3.20 (dd, 1H, J=17.1, 7.3 Hz), 4.74 (dd, 1H, J=7.3, 6.8 Hz), 7.29 (d, 2H, 8.3 Hz), 7.36 (d, 2H, 8.3 Hz)

$^{13}$C-NMR (δ (ppm), D$_2$O+DCl): 23.4, 40.7, 54.4, 130.0, 133.0, 135.0, 143.1, 176.3
MS (EI) m/z: 179 (M$^+$)
MS (CI, i-C$_4$H$_{10}$) m/z: 180 (MH$^+$)
Elemental analysis; Calcd: C, 67.02%; H, 7.31%; N, 7.82%
Found: C, 67.05%; H, 7.40%; N, 7.66%

Reference Example 6 (Synthesis of ethyl 3-amino-3-(4-tolyl)propionate (racemic mixture))

To 660 mL (11.3 mol) of ethanol were added 132 g (179 mmol) of 3-amino-3-(4-tolyl)propionic acid (racemic mixture) synthesized in Reference example 5 and 86.7 g (884 mmol) of conc. sulfuric acid, and the mixture was reacted under stirring at 60° C. for 4 hours. After completion of the reaction, the obtained reaction mixture was concentrated under reduced pressure, and added thereto 6 mol/L aqueous sodium hydroxide solution to adjust a pH of the reaction mixture to 8.5. Then, 800 mL of ethyl acetate and 300 mL of water were added thereto to extract the mixture, and the organic layer was dried over anhydrous magnesium sulfate. After filtration, the filtrate was concentrated under reduced pressure to obtain 130 g (Isolation yield based on 3-amino-3-(4-tolyl)propionic acid (racemic mixture): 85.0%) of ethyl 3-amino-3-(4-tolyl)propionate (racemic mixture) as colorless liquid.

Incidentally, physical properties of the ethyl 3-amino-3-(4-tolyl)propionate (racemic mixture) were as follows.
$^1$H-NMR (δ (ppm), CDCl$_3$): 1.20 (t, 3H, J=7.3 Hz), 2.36 (s, 3H), 3.11 (dd, 1H, J=7.8, 16.6 Hz), 3.26 (dd, 1H, J=6.3, 16.6 Hz), 4.11-4.18 (m, 2H), 4.82 (dd, 1H, J=6.3, 7.8 Hz), 7.35 (d, 2H, J=7.8 Hz), 7.42 (d, 2H, J=8.3 Hz)
$^{13}$C-NMR (δ (ppm), CDCl$_3$): 16.1, 23.1, 41.1, 54.2, 65.2, 129.9, 132.8, 134.9, 142.9, 174.3

Example 8 (Synthesis of (S)-3-amino-3-(4-tolyl) propionic acid and ethyl (R)-3-amino-3-(4-tolyl) propionate)

To 2.5 mL of t-butylmethyl ether to which water had been saturated were added 500 mg (2.41 mmol) of ethyl 3-amino-3-(4-tolyl)propionate (racemic mixture) and 25.0 mg of lipase (Amano Lipase PS (trade name); available from Aldrich) originated from *Burkholderia cepacia* (*Pseudomonas cepacia*), and the mixture was maintained at 30° C. To the resulting mixture was added 43.4 μL of water at the same temperature, and the mixture was reacted under stirring at 30° C. for 52 hours. Amano Lipase PS was substantially suspended state during the reaction, and with the progress of the reaction, (S)-3-amino-3-phenylpropionic acid which is a product was precipitated as a crystalline solid. After completion of the reaction, 0.5 mL of acetone was added to the reaction mixture and the resulting mixture was filtered to obtain a mixture containing 175 mg (Isolation yield based on ethyl 3-amino-3-(4-tolyl)propionate (racemic mixture)= 40.5%) of (S)-3-amino-3-(4-tolyl)propionic acid and lipase.

When optical purity of the (S)-3-amino-3-(4-tolyl)-propionic acid was measured by using high performance liquid chromatography which uses an optically active column, then it was 99.8% ee.

The ethyl (R)-3-amino-3-(4-tolyl)propionate was led to ethyl (R)-3-(2-furoylamino)-3-(4-tolyl)propionate according to the conventional manner, and an optical purity thereof was measured by using high performance liquid chromatography which uses an optically active column, then it was 84.0% ee.

Incidentally, the E value in the present reaction was 3454.

Analytical conditions of high performance liquid chromatography;

Optically active 3-amino-3-(4-tolyl)propionic acid

Column: Chiral CD-Ph (0.46 cmΦ×25 cm×2 columns connected, available from Shiseido Co., Ltd.)

Solvent: acetonitrile/water (=5/95 (volume ratio))
Potassium dihydrogen phosphate 40 mmol/L
Adjusted to pH 3.5 with phosphoric acid Flow rate: 0.5 mL/min Temperature: 30° C.

Wavelength: 220 nm

Optically active ethyl 3-(2-furoylamino)-3-(4-tolyl)propionate

Column: Chiralcel OJ-H (0.46 cmΦ×25 cm, available from Daicel Chemical Industries, Ltd.)

Solvent: hexane/isopropyl alcohol (=9/1 (volume ratio))

Flow rate: 0.5 mL/min

Temperature: 30° C.

Wavelength: 220 nm

Also, physical properties of the (S)-3-amino-3-(4-tolyl) propionic acid were the same as those shown in Reference example 5, and physical properties of the ethyl (R)-3-amino-3-(4-tolyl)propionate were the same as those shown in Reference example 6.

UTILIZABILITY IN INDUSTRY

The present invention relates to a process for preparing an optically active (S or R)-β-amino acid and an optically active (R or S)-β-amino acid ester from a β-amino acid ester (racemic mixture) simultaneously. These optically active β-amino acid and an ester thereof are useful as a starting material or a synthetic intermediate for a physiologically active peptide or lactam series antibiotics.

The invention claimed is:

1. A process for preparing an optically active (S or R)-β-amino acid represented by the formula (II):

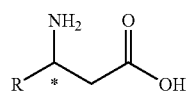

wherein R represents an aryl group which may have a substituent(s), and * represents an asymmetric carbon atom, and an optically active (R or S)-β-amino acid ester represented by the formula (III):

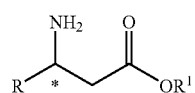

wherein R has the same meaning as defined above, $R^1$ represents an alkyl group which may have a substituent(s), and * represents an asymmetric carbon atom, provided that it has a reverse absolute configuration to that of the compound of the formula (II), which comprises selectively reacting water and one of enantiomers of a β-amino acid ester represented by the formula (I):

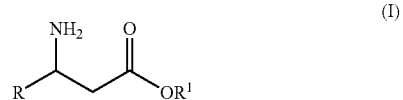

wherein R and $R^1$ have the same meanings as defined above, which is a racemic mixture, in the presence of a lipase in an organic solvent, wherein water is present in an amount equal to, or less than, its solubility in the organic solvent.

2. The process according to claim 1, wherein the amount of water to be used is 0.5 to 10 mol based on 1 mol of the β-amino acid ester which is a racemic mixture.

3. The process according to claim 1, wherein the lipase is a lipase originated from *Burkholderia cepacia*(*Pseudomonas cepacia*).

4. The process according to claim 1, wherein at least one selected from an inorganic salt selected from sodium phosphate and potassium phosphate, or an organic salt selected from sodium acetate, ammonium acetate and sodium citrate is present in a reaction system.

5. The process according to claim 1, wherein the lipase is lyophilized in the presence of a buffer.

6. The process according to claim 5, wherein the buffer is at least one buffer selected from the group consisting of an aqueous sodium phosphate solution, an aqueous potassium phosphate solution and an aqueous ammonium acetate solution.

7. The process according to claim 1, wherein at least one surfactant selected from the group consisting of a nonionic surfactant, an amphoteric surfactant, an anionic surfactant and a cationic surfactant is present.

8. The process according to claim 1, wherein $R^1$ is a methyl group or ethyl group each of which may have a substituent(s).

9. The process according to claim 8, wherein $R^1$ is a group substituted by a halogen atom or an alkoxyl group.

10. The process according to any one of claims 1 to 2 and 3 to 9, wherein the organic solvent is at least one organic solvent selected from the group consisting of an ether, a ketone, an aliphatic hydrocarbon and an aromatic hydrocarbon.

11. The process according to claim 1, wherein an optically active (S or R)-β-amino acid represented by the formula (II):

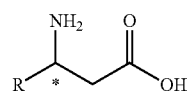

wherein R represents an aryl group which may have a substituent(s), and $R^1$ represents an alkyl group which may have a substituent(s), and * represents an asymmetric carbon atom, and an optically active (R or S)-β-amino acid ester represented by the formula (III):

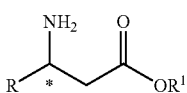

wherein R and $R^1$ have the same meanings as defined above, * represents an asymmetric carbon atom, provided that it has a reverse absolute configuration to that of the compound of the formula (II), produced by the reaction are each isolated from the mixture thereof.

12. The process according to claim 1, wherein R is a phenyl group which may have a substituent(s).

13. The process according to claim 3, wherein R is a phenyl group or a tolyl group.

14. The process according to claim 1, wherein the amount of water to be used is 0.5 to 5.0 mol based on 1 mol of the β-amino acid ester which is a racemic mixture.

15. The process according to claim 1, wherein the amount of water to be used is 1.0 to 3.0 mol based on 1 mol of the β-amino acid ester which is a racemic mixture.

16. The process according to claim 1, wherein the amount of water to be used is 1.5 to 2.5 mol based on 1 mol of the β-amino acid ester which is a racemic mixture.

17. The process according to claim 1, wherein the organic solvent is at least one selected from the group consisting of n-hexane, n-heptane, cyclopentane, cyclohexane, toluene, diisopropyl ether, t-butyl methyl ether, cyclopentylmethyl ether and tetrahydrofuran.

18. The process according to claim 1, wherein the organic solvent is at least one selected from the group consisting of n-hexane, cyclohexane, toluene, diisopropyl ether, t-butyl methyl ether and cyclopentylmethyl ether.

19. The process according to claim 1, wherein the organic solvent is at least one selected from the group consisting of cyclohexane, toluene and t-butyl methyl ether.

* * * * *